United States Patent
Barbera

[19]

[11] Patent Number: 5,355,182
[45] Date of Patent: Oct. 11, 1994

[54] GOLFING SPECTACLES

[75] Inventor: Umberto Barbera, Turin, Italy

[73] Assignee: Newtel S.r.l., Turin, Italy

[21] Appl. No.: 868,660

[22] Filed: Apr. 15, 1992

[30] Foreign Application Priority Data

Apr. 15, 1991 [IT] Italy ............... T091U000085

[51] Int. Cl.⁵ ................................................ G02C 7/16
[52] U.S. Cl. ........................................ 351/45; 351/165
[58] Field of Search ................... 351/44, 45, 46, 47,
351/163, 165; 273/187.2; 2/12, 13, 15, 432, 433

[56] References Cited

U.S. PATENT DOCUMENTS

| | | | |
|---|---|---|---|
| 1,676,760 | 7/1928 | Wilson | 351/45 |
| 2,230,009 | 1/1941 | Ordorica | 351/45 |
| 2,445,153 | 7/1948 | Rearick | 351/45 |
| 3,819,189 | 6/1974 | Goode | 273/187.2 |
| 4,311,368 | 1/1982 | Saito et al. | 351/45 |
| 4,338,003 | 7/1982 | Adrian | 351/45 |

FOREIGN PATENT DOCUMENTS

| | | | |
|---|---|---|---|
| 2229600 | 1/1974 | Fed. Rep. of Germany | 351/45 |
| 1000379 | 2/1952 | France | 351/44 |
| 2469734 | 5/1981 | France | 351/45 |
| 7712825 | 5/1979 | Netherlands | 351/45 |
| 719709 | 12/1954 | United Kingdom | 351/45 |

Primary Examiner—Ricky D. Shafer
Attorney, Agent, or Firm—Sughrue, Mion, Zinn, Macpeak & Seas

[57] ABSTRACT

A pair of spectacles to be worn by a golfer to facilitate the alignment of a golf ball with a target includes two optical elements supported by a spectacle frame a having a ark, tinted upper region and a clear lower region. The regions are separated by two parallel but non-aligned lines, each inclined to the horizontal by between 5° and 15°. The lines are oriented downwardly from left to right, as seen from outside the spectacles, in a pair of spectacles for a right-handed person and from right to left in a pair of spectacles for a left-handed person. The two lines are situated in front of respective eyes when the spectacles are in use and are offset vertically relative to each other by a distance of the order of 2 mm.

2 Claims, 2 Drawing Sheets

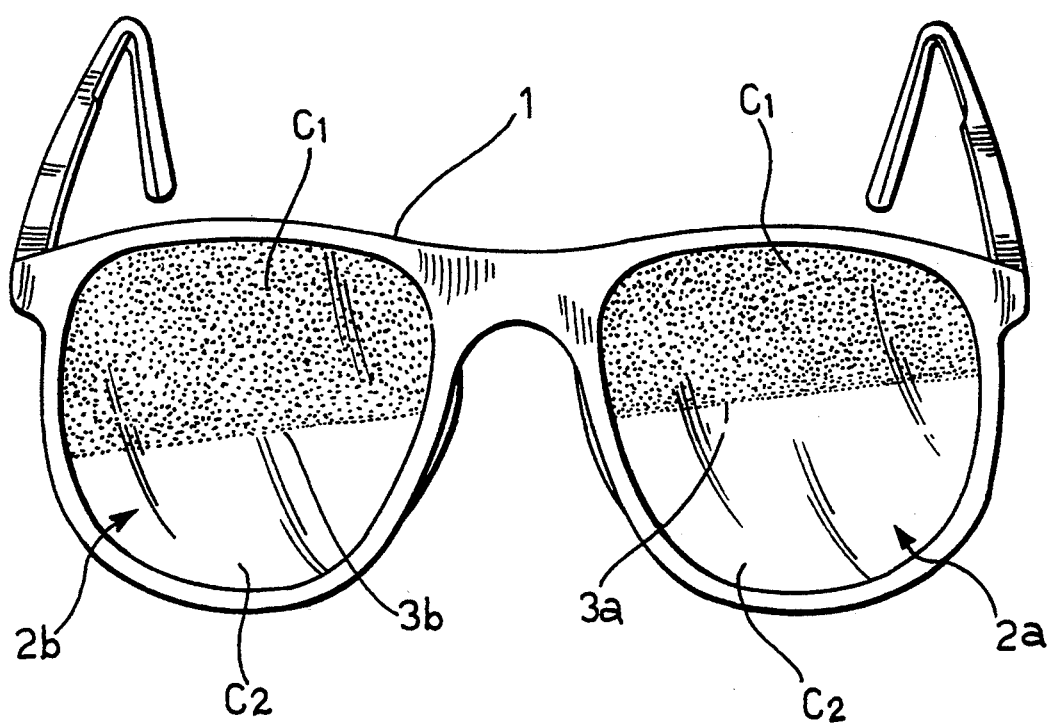

GOLFING SPECTACLES

BACKGROUND OF THE INVENTION

The present invention relates to a pair of spectacles to be worn by a golfer to facilitate the alignment of a golf ball with a target.

In a pair of spectacles known from U.S. Pat. No. 3,264,002, in order to achieve this object, the transparent optical means carried by the spectacle frame have an opaque horizontal line, that is, a line parallel to a tangent of the upper edges of the frame, so that a player wearing the spectacles sees a hazy, dark, guide line between the ball and the target which, in this case, is represented by the hole in a green.

In a similar pair of spectacles known from U.S. Pat. No. 4,991,849, the transparent optical means are tinted like a sun filter and carry a clear horizontal line which may be constituted by grooves cut in the surfaces of the lenses or by a thin, untinted strip of the optical means, produced by the application of a mask in that region during the tinting of the optical means. The spectacles described in this patent also have a device for adjusting the distance between the bridge which carries the lenses and the rest of the frame in order to adjust the distance between the clear line and the golfer's eyes.

A first disadvantage of these known solutions lies in the fact that, in practice, the player cannot focus on a thin, clear or dark line carried by the optical means of the spectacles and thus see it clearly (as, after all, is admitted in the description of the U.S. Pat. No. 3,264,002) and this causes discomfort to the person wearing the spectacles.

A further disadvantage of these known solutions lies in the fact that, particularly when the golfer is executing a "drive", he has to arrange himself parallel to an imaginary line linking the ball and the target; as he moves his arms before making the stroke, however, a right-handed player naturally tends to turn his head to the right as he focuses his eyes on the ball so that, as he effects the stroke, the attitude of his body diverges from the imaginary line by an angle which, in practice, varies between 5° and 15°.

Since, in the spectacles known from the two patents cited above, the lines carried by the optical means for facilitating the alignment of the ball and the target are horizontal, the lines follow the movement of the user's head and hence cannot give him a correct indication of the alignment of the ball and the target.

SUMMARY OF THE INVENTION

In order to prevent these problems, the subject of the present invention is a pair of spectacles to be worn by a golfer to facilitate the alignment of a golf ball with a target, including:
  a spectacle frame,
  optical means supported by the frame and comprised of two elements each having a dark, tinted upper region and a clear lower region, the regions being separated by two parallel but non-aligned lines, each inclined to the horizontal by between 5° and 15°,
  each line being oriented downwardly from left to right, as seen from outside the spectacles, in a pair of spectacles for a right-handed person and from right to left in a pair of spectacles for a left-handed person,
  one of the two lines being situated in front of the right eye and the other of the two lines being situated in front of the left eye when the spectacles are in use with one of the lines being offset upwardly from the other line by a distance of the order of 2 mm.

When using a pair of spectacles according to the invention, a golfer perceives the difference in the colouration of the two regions of the optical means as an oblique line which is disposed horizontally when the player inclines his head to the right, automatically compensating for the inclination of his head and thus providing the player with a correct alignment of the ball with the target.

Moreover, tests carried out have shown that the fact that the two lines are parallel but slightly offset enables the player to focus upon the lines as if they were a continuous line without experiencing the discomfort caused by the continuous light or dark lines in the known solutions.

This phenomenon may be assumed to be due to the fact that the non-alignment of the two lines acts as a corrector for facilitating the focusing of the lenses of the player's eyes on the ball and on the planes of the spectacle lenses in succession.

BRIEF DESCRIPTION OF THE DRAWINGS

The invention will now be described with reference to the appended drawings, provided purely by way of non-limiting example, in which:

FIG. 3 shows a variant of FIG. 2.

DETAILED DESCRIPTION OF THE INVENTION

Figure 1:
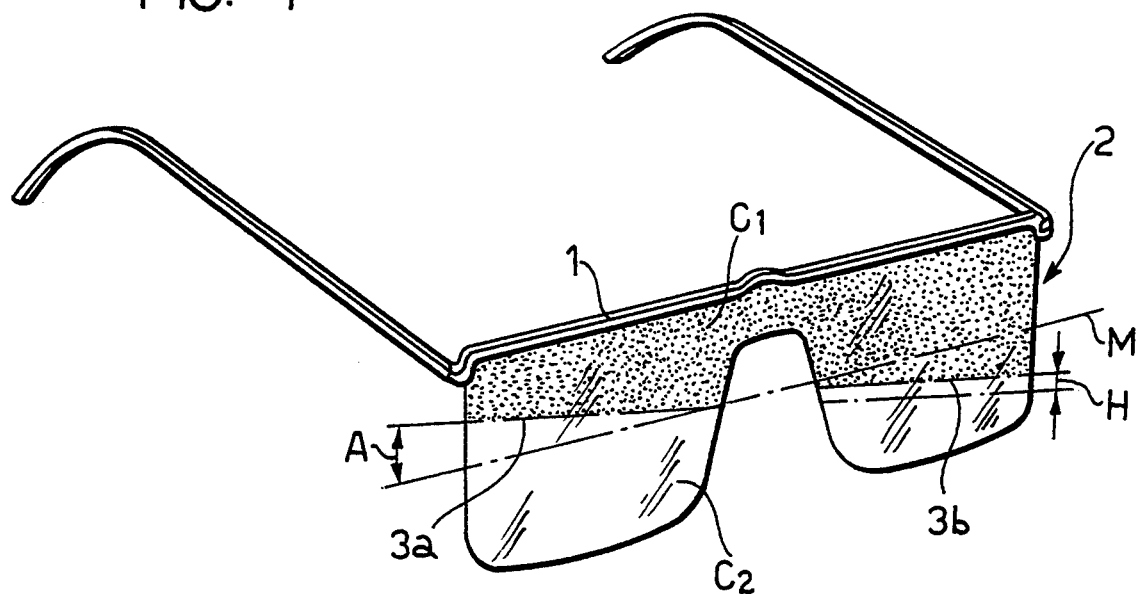
FIG. 1 is a perspective view of a pair of spectacles according to the invention.

In the embodiment of FIG. 1, the frame of a pair of spectacles is indicated 1 and the optical means supported by the frame and constituted by two interconnected elements, are indicated 2.

The optical means 2 have an upper region $C_1$ with a dark tint, preferably in the manner of a sun filter, and a clear lower region $C_2$.

The regions $C_1$ and $C_2$ are separated by two non-aligned lines 3a and 3b.

The two lines 3a and 3b are inclined to a horizontal line M, that is, to a line parallel to the upper edge of the optical element 2, by an angle A of between 5° and 15° and are offset slightly from each other in the vertical direction, preferably by a distance H of the order of 2 mm. The line M divides the optical element 2 into an upper portion above the line M and a lower portion below the line M.

The pair of spectacles shown is intended for a right-handed person and the lines 3a, 3b are thus oriented downwardly from left to right as seen from outside the spectacles.

The line 3b, that is, the portion which extends through the lower portion of the optical means is preferably offset vertically upwardly relative to the line 3a.

Figure 2:
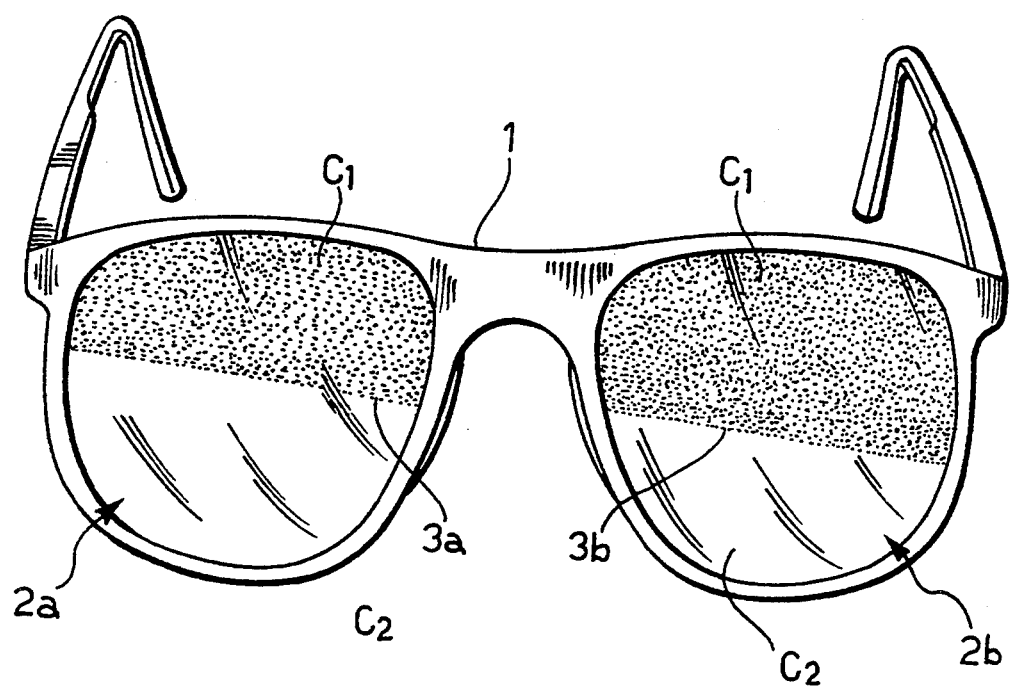
FIG. 2 is a front view of a pair of spectacles according to a variant of FIG. 1.

The spectacles shown in FIG. 2 differ from those shown in FIG. 1 in that the optical means comprise two separate elements 2a, 2b, each of which is constituted by a glass or lens and which are housed in two seats in the frame 1.

The pair of spectacles shown in FIG. 3 differs from that shown in FIG. 2 in that it is intended for a left-handed person and the lines 3a, 3b have an opposite orientation from that of the embodiments of FIGS. 1 and 2. In fact, the line is inclined downwardly from right to left as seen from outside the spectacles.

What is claimed is:

1. A pair of spectacles to be worn by a golfer to facilitate the alignment of a golf ball with a target, including:

a spectacle frame, and two lens elements supported by the frame, each of said two lens elements each having a dark, tinted upper region and a clear lower region, the tinted upper region of one lens being greater in area than the tinted upper region of the other lens with the regions being separated by two parallel but non-aligned lines, each inclined to the horizontal by between 5° and 15°, each line being oriented downwardly from left to right, as seen from outside the spectacles, in a pair of spectacles for a right-handed person and from right to left in a pair of spectacles for a left-handed person, one of the two lines being situated in front of the right eye and the other of the two lines being situated in front of the left eye when the spectacles are in use with one of the lines being offset upward of the other line by a distance of the order of 2 mm.

2. A pair of spectacles to be worn by a golfer to facilitate the alignment of a golf ball with a target, including:

a spectacle frame, and a single optical element supported by the frame, said optical element being comprised of two interconnected lens elements each having a dark tinted upper region and a clear lower region, the tinted upper region of one lens being greater in area than the tinted upper region of the other lens with the regions being separated by two parallel but non-aligned lines, each inclined to be horizontal by between 5 degrees and 15 degrees, each line being oriented downwardly from left to right, as seen from outside the spectacles, in a pair of spectacles for a right-handed person and from right to left in a pair of spectacles for a left-handed person, one of the two lines being situated in front of the right eye and the other of the two lines being situated in front of the left eye when the spectacles are in use with one of the lines being offset upward of the other line by a distance of the order of 2 mm.

* * * * *